United States Patent
Bolling et al.

(10) Patent No.: US 7,022,400 B2
(45) Date of Patent: Apr. 4, 2006

(54) METHOD OF PROVIDING FLOW CONTROL OF HEAT ACTIVATED SEALANT USING A COMBINATION SEALANT/FLOW CONTROL AGENT

(75) Inventors: Richard Bolling, Brooklyn, MI (US); Michael E. Speicher, Evansville, IN (US); David Williams, Evansville, IN (US)

(73) Assignee: Adco Products, Inc., Michigan Center, MI (US)

( * ) Notice: Subject to any disclaimer, the term of this patent is extended or adjusted under 35 U.S.C. 154(b) by 182 days.

(21) Appl. No.: 09/756,453

(22) Filed: Jan. 8, 2001

(65) Prior Publication Data

US 2001/0051665 A1 Dec. 13, 2001

Related U.S. Application Data

(60) Provisional application No. 60/175,092, filed on Jan. 7, 2000.

(51) Int. Cl.
*B32B 7/02* (2006.01)

(52) U.S. Cl. ............... 428/212; 428/626; 428/457; 428/522

(58) Field of Classification Search ............ 428/304.4, 428/343, 346, 347, 348, 349, 355 EN, 355 BL, 428/500, 212, 626, 457, 522
See application file for complete search history.

(56) References Cited

U.S. PATENT DOCUMENTS

| | | | | |
|---|---|---|---|---|
| 4,320,076 A | * | 3/1982 | Greenwood | 264/35 |
| 4,529,740 A | * | 7/1985 | Trainor | 521/81 |
| 4,803,117 A | * | 2/1989 | Daponte | 428/326 |
| 5,211,792 A | | 5/1993 | Carter | |
| 5,344,208 A | * | 9/1994 | Bien et al. | 296/187 |
| 5,424,115 A | * | 6/1995 | Stokes | 428/198 |
| 5,731,069 A | * | 3/1998 | Delle Donne et al. | 428/215 |
| 5,964,979 A | * | 10/1999 | George et al. | 156/309.6 |
| 6,030,701 A | * | 2/2000 | Johnson et al. | 428/343 |
| 6,287,669 B1 | * | 9/2001 | George et al. | 428/156 |
| 6,485,589 B1 | | 11/2002 | Johnson et al. | |

* cited by examiner

*Primary Examiner*—Melanie Bissett
(74) *Attorney, Agent, or Firm*—Dinsmore & Shohl LLP

(57) ABSTRACT

A method of controlling the flow of a heat activated expandable sealant is provided in which a heat activated sealant is coated with a flow control agent having a melt flow rate which is lower than that of the sealant. The combination sealant/flow control agent is preferably used to seal gaps or cavities in parts such as components in automotive vehicles with minimal sagging.

12 Claims, 2 Drawing Sheets

METHOD OF PROVIDING FLOW CONTROL OF HEAT ACTIVATED SEALANT USING A COMBINATION SEALANT/FLOW CONTROL AGENT

CROSS REFERENCE TO RELATED APPLICATIONS

This application claims the benefit of U.S. provisional application Ser. No. 60/175,092, filed Jan. 7, 2000.

BACKGROUND OF THE INVENTION

This invention is directed to a method for providing flow control of heat activated expandable or non-expandable sealants which are used to seal gaps or cavities in parts such as components in automotive vehicles, and more particularly, to such a method which utilizes a sealant in combination with a flow control agent to modulate the flow of the sealant upon heating.

In the manufacture of automotive vehicles, many body components include cavities which require sealing in order to block the passage of dust, moisture, and air (fumes) which can cause corrosion of the body parts. Such sealants are also used to block the passage of noise through the openings. Heat activated sealants are known in the automotive industry for the purpose of filling such gaps and voids. For example, expandable sealants may be formed into a desired configuration which is adapted to be placed within a body cavity or between two parts so that when the part is subjected to a paint baking operation or other process at elevated temperatures, the shaped sealant expands to an extent that the cavity or area between the parts is filled or sealed. Such heat activated sealants are typically comprised of thermoplastic or thermosetting materials which may contain a blowing agent which is activated upon heating such that the sealant expands and flows into the gaps.

Heat activated expandable sealants currently in use are typically used to bridge or seal gaps which are less than about 8 to 10 mm. However, when such gaps are greater than about 10 mm (up to 100 mm), it is difficult to achieve proper flow as the adhesive tends to flow excessively, causing unsightly "stalactites". In addition, the sealant is often unable to expand or flow sufficiently to bridge the larger gaps without excess thinning or blow-out in the gap being sealed.

It would be desirable to be able to better control the flow of heat activated sealants to eliminate the problems of excessive flow or sag. Accordingly, there is a need in the art for a method of controlling flow of heat activated sealants.

SUMMARY OF THE INVENTION

The present invention meets that need by providing a flow control agent for use in combination with a heat activated expandable sealant for the purpose of controlling the flow of the sealant upon heating. The sealant/flow control agent combination may be used to seal cavities or gaps in parts such as automotive components with minimal sagging.

In accordance with one aspect of the present invention, a method for controlling the flow of a heat activated expandable sealant is provided which comprises providing a heat activated expandable sealant, applying a flow control agent to at least a portion of the sealant, and heating the sealant with the flow control agent to cause the sealant to flow. The sealant has a higher melt flow rate than the flow control agent, i.e., the flow control agent is more resistant to flow than the sealant, which allows the flow to be controlled upon heating. By "melt flow rate" (also referred to as melt flow index or melt flow number), it is meant the output rate (flow) of molten resin in grams which would occur in 10 minutes through a standard die of 2.095 mm in diameter and 8.0 mm in length under the action of a standard weight of 2.16 kg at a temperature of 190° C. (see ASTM Standard 1238).

The melt flow rate of the sealant is greater than the melt flow rate of the flow control agent.

The expandable sealant of the present invention is preferably in the form of a tack-free, rubber/plastic extruded sheet or thermoformed (shaped) part. The sealant may be thermoformed prior to or after applying the flow control agent.

The flow control agent is preferably in the form of a liquid coating which is coated on one side of the shaped sealant. In an alternative embodiment, the flow control agent may be in the form of a mesh, film or any other material which controls the amount of flow of the sealant as described above.

A number of sealants and flow control coatings may be used in the present invention as long as they satisfy the above-described melt flow rate relationship. Accordingly, it should be appreciated that both the sealant and flow control coating may be selected from the group consisting of acrylic resins, styrene-butadiene block copolymers, isoprene butadiene block copolymers, ester gums, ethylene propylene diene rubber, ethylene vinyl acetate, hydrocarbon resins, phenolic resins, polyamides, polyethylene, polyesters, polyolefins, polypropylene, polyvinyl acetate, polyvinylidene chloride, polyvinyl chloride, styrene butadiene, terpolymers, and vinyl acetate.

The expandable sealant also preferably includes a blowing agent which causes the sealant to expand during heating. The sealant may also include fillers, plasticizers, and curing agents. In a preferred embodiment, the heat activated expandable sealant comprises modified polyethylene, a styrene-butadiene copolymer, a hydrocarbon resin, ethylene vinyl acetate, and a blowing agent.

The flow control agent preferably comprises a polyvinyl acetate.

In use, the sealant with the flow control agent is positioned or secured over the cavity of a component and heated to a temperature of between about 250° F. to 400° F. (121° C. to 204° C.) to cause the sealant to flow into and seal the cavity. The use of the flow control agent in combination with the sealant allows the sealant, upon heating, to bridge gaps or cavities in parts that are up to 100 mm and with less sagging than the use of a sealant alone.

Accordingly, it is a feature of the invention to provide a method for controlling the flow of an expandable sealant. This, and other features and advantages of the present invention, will become apparent from the following detailed description, accompanying drawings, and appended claims.

DETAILED DESCRIPTION OF THE PREFERRED EMBODIMENTS

The present invention provides a number of advantages over previously used heat activated sealants. By utilizing a flow control agent in combination with the sealant which has a greater resistance to flow than the sealant, the amount of flow of the sealant is minimized and controlled such that no excessive flow or thinning occurs.

In a preferred embodiment of the invention, the sealant is an expandable sealant comprising a modified polyethylene, a styrene-butadiene copolymer, a hydrocarbon resin, and ethylene vinyl acetate. Examples of such preferred expandable sealants for use in the present invention include RV7172-3, RV7076-3, RV7113-3, and RV7168-3, all commercially available from RuVan Inc. Additional sealants suitable for use in the present invention are also commercially available from RuVan Inc.

While the invention has been described herein primarily with reference to expandable sealants, it should be appreciated that the flow control agent may also be used in combination with non-expandable sealants. An example of a non-expandable sealant is RV7148-3, commercially available from RuVan Inc.

Preferred flow control coatings for use in the present invention include latex vinyl chloride house paint, modified (compounded) vinyl-acetate polymers and copolymers, natural rubber latex, synthetic elastomeric polymers such as styrene-butadiene, chloroprene, or nitrile rubbers. More preferred flow control coatings are ethylene-acetate/ethylene vinyl acetate copolymers available from Air Products under the designations Airflex 300 and 400.

In the preferred method of the present invention in which the sealant is used in an automotive application, the flow control coating is coated over the shaped sealant on at least one side (preferably the side which will be exposed to air) and allowed to dry at ambient temperature or by warm forced air drying. The coating is preferably applied at a dry coating weight of greater than 1.5 g/m$^2$ but less than 50 g/m$^2$ of dry coating (with about 1.5–3 mm sheet thickness of the sealant material).

The shaped sealant with the flow control coating on its surface is then secured to the desired automotive part as desired by mechanical fixing, by the use of a pressure sensitive adhesive, or by simply placing the sealant in the desired position. The shaped sealant positioned on the part is then processed through a paint bake cycle at a temperature of between about 250° F. to 400° F. (121° C. to 204° C.) for between about 10 to 60 minutes.

While the preferred method of the invention is to apply the flow control coating after the sealant has been extruded or thermoformed to the desired shape, it should also be appreciated that the coating may also be easily applied prior to the thermoforming operation. In this method, the heat from the thermoforming operation aids in adhering the flow control coating to the sealant and to dry or cure it so that the resulting shaped sealant components may be stacked prior to use.

Figure 1:
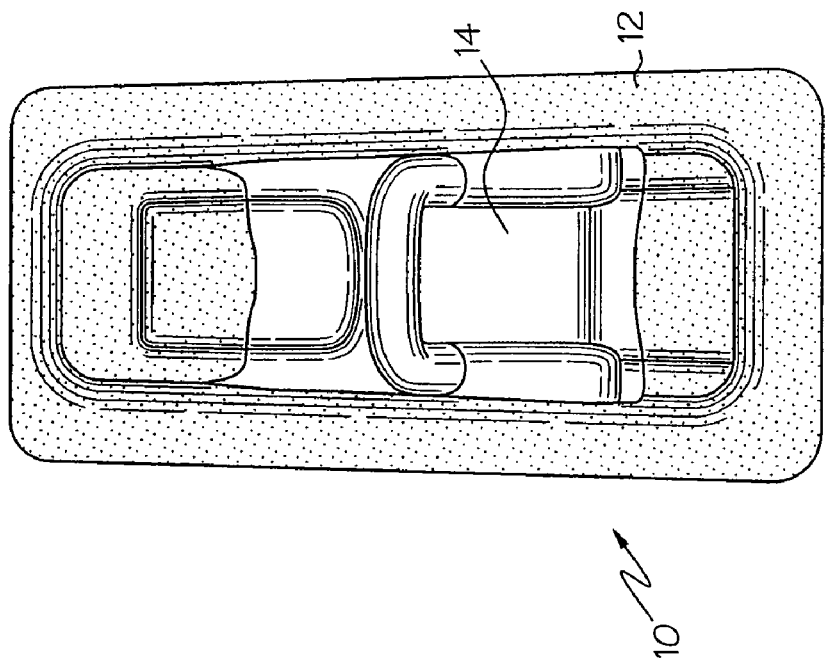
FIG. 1 illustrates a shaped sealant in accordance with the present invention.
Figure 2:
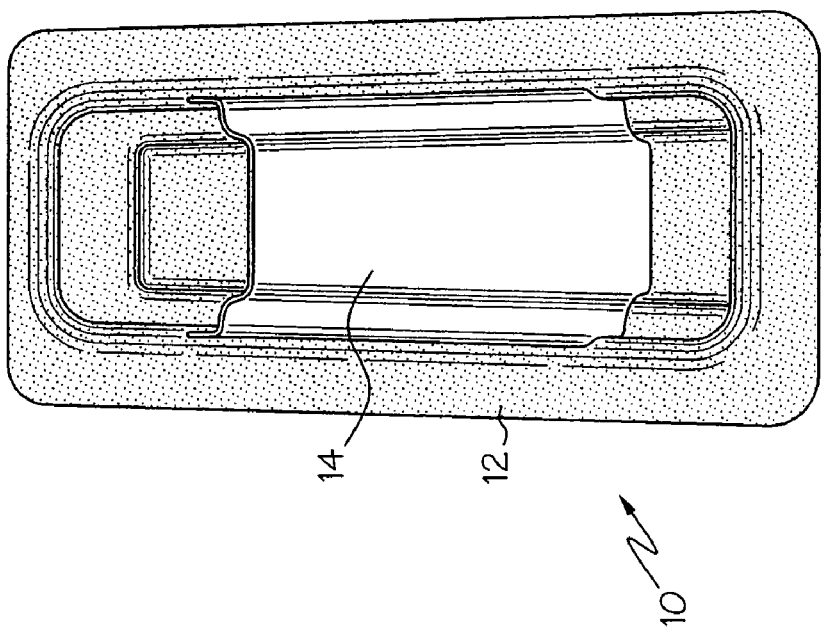
FIG. 2 illustrates the shaped sealant coated with a flow control coating which has been secured to an automotive part and subjected to a paint bake cycle.

In a preferred application, the sealant is shaped to form a pocket sealer for use in sealing holes in the body components of vehicles. FIGS. 1 and 2 illustrate this use of the invention. FIG. 1 illustrates the shaped pocket sealer 10 comprised of the expandable sealant 12 on a metal automotive part 14. FIG. 2 illustrates the pocket sealer 10 with the expandable sealant and flow control coating on its surface after it has been secured to a cavity on the body of the vehicle and baked for 20 minutes at 325° F. (163° C.).

Figure 3:
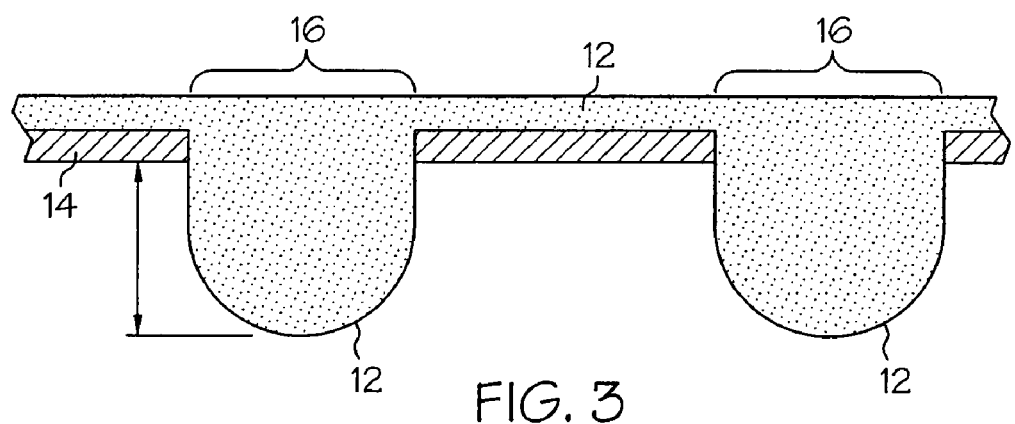
FIG. 3 illustrates the sag which occurs during heating of the sealant without the use of a flow control agent.
Figure 4:
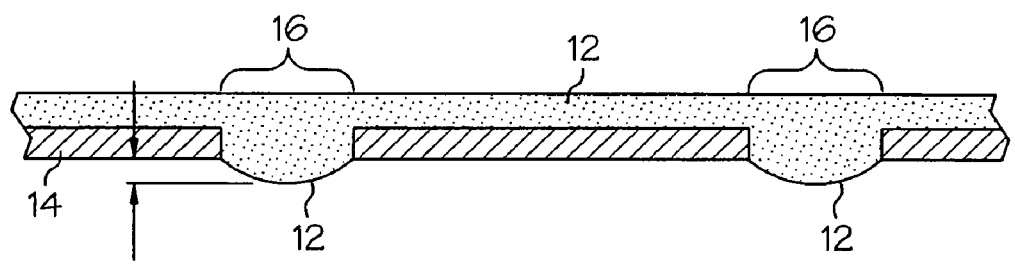
FIG. 4 illustrates the minimal sag which occurs with the use of a flow control agent.

FIGS. 3 and 4 illustrate the improved flow control obtained by using the flow control agent of the present invention. FIG. 3 illustrates the sag which occurs when the expandable sealant 12 is applied over cavities 16 and heated without the use of a flow control agent. FIG. 4 illustrates the sag which occurs when a flow control agent is used in combination with the expandable sealant. As can be seen, minimal sag occurs with the use of the flow control agent.

While certain representative embodiments and details have been shown for purposes of illustrating the invention, it will be apparent to those skilled in the art that various changes in the methods and apparatus disclosed herein may be made without departing from the scope of the invention, which is defined in the appended claims.

The invention claimed is:

1. A combination consisting of a heat activated expandable sealant and a flow control agent directly contacting and covering at least a portion of the surface of said sealant, said combination overlying a gap or cavity in a substrate with said sealant directly contacting said substrate; wherein said heat activated expandable sealant has a melt flow rate which is higher than the melt flow rate of said flow control agent; and wherein said heat activated expandable sealant has been heated to a temperature sufficient to cause said sealant to flow into and seal said gap or cavity; and wherein said heat activated expandable sealant with said flow control agent exhibits less sagging over said gap or cavity than a heat activated expandable sealant without said flow control agent.

2. The combination of claim 1 wherein said flow control agent comprises polyvinyl acetate.

3. The combination of claim 1 wherein said heat activated expandable sealant is in the form of an extruded sheet or thermoformed part.

4. The combination of claim 1 Wherein said heat activated expandable sealant and said flow control agent have been heated to a temperature between about 250° F. to 400° F.

5. The combination of claim 1 wherein said flow control agent is in the form of a mesh or film.

6. The combination of claim 1 wherein said flow control agent is in the form of a dry coating which has been applied to said sealant as a liquid coating.

7. A combination consisting of a heat activated expandable sealant and a flow control agent directly contacting and covering at least a portion of the surface of said sealant, said combination overlying a gap or cavity in a substrate with said sealant directly contacting said substrate; wherein said heat activated expandable sealant includes a blowing agent and said sealant has been heated to a temperature sufficient to cause said sealant to flow into and seal said gap or cavity; and wherein said heat activated expandable sealant has a melt flow rate which is higher than the melt flow rate of said flow control agent.

8. The combination of claim 7 wherein said sealant is in the form of a thermoformed part.

9. The combination of claim 8 wherein said thermoformed part comprises a pocket sealer.

10. A combination consisting of a heat activated expandable sealant and a flow control agent directly contacting and covering at least a portion of the surface of said sealant, said flow control agent comprising polyvinyl acetate, said combination overlying and sealing a gap or cavity in a substrate with said sealant directly contacting said substrate; wherein said heat activated expandable sealant has a melt flow rate which is higher than the melt flow rate of said flow control agent.

11. A combination consisting of a heat activated expandable sealant in the form of a thermoformed part and a flow control agent directly contacting and covering at least a portion of the surface of said sealant said combination overlying and sealing a gap or cavity in a substrate with said sealant directly contacting said substrate; said heat activated expandable sealant having a melt flow rate which is higher than the melt flow rate of said flow control agent.

12. A combination consisting of a heat activated expandable sealant and a flow control agent directly contacting and covering at least a portion of the surface of said sealant, said combination overlying and sealing a gap or cavity in substrate with said sealant directly contacting said substrate; wherein said heat activated expandable sealant has a melt flow rate which is higher than the melt flow rate of said flow control agent.

* * * * *

UNITED STATES PATENT AND TRADEMARK OFFICE
CERTIFICATE OF CORRECTION

PATENT NO. : 7,022,400 B2
APPLICATION NO. : 09/756453
DATED : January 26, 2005
INVENTOR(S) : Bolling et al.

It is certified that error appears in the above-identified patent and that said Letters Patent is hereby corrected as shown below:

Col. 4, line 37 "Wherein" should read --wherein--;

Col. 4, line 39 "250° F." should read --250° F--; and

Col. 5, line 6 "sealant" should read --sealant,--

Signed and Sealed this

Nineteenth Day of September, 2006

JON W. DUDAS
*Director of the United States Patent and Trademark Office*

UNITED STATES PATENT AND TRADEMARK OFFICE
CERTIFICATE OF CORRECTION

PATENT NO. : 7,022,400 B2
APPLICATION NO. : 09/756453
DATED : April 4, 2006
INVENTOR(S) : Bolling et al.

It is certified that error appears in the above-identified patent and that said Letters Patent is hereby corrected as shown below:

Col. 4, line 37 "Wherein" should read --wherein--;

Col. 4, line 39 "250° F." should read --250° F--; and

Col. 5, line 6 "sealant" should read --sealant,--

This certificate supersedes Certificate of Correction issued September 19, 2006.

Signed and Sealed this

Twenty-fourth Day of October, 2006

JON W. DUDAS
*Director of the United States Patent and Trademark Office*